United States Patent [19]

Ferrari

[11] 4,198,344

[45] Apr. 15, 1980

[54] PROCESS FOR THE PREPARATION OF POLYHYDROXYLATED STEROIDS, LYSERGOL AND ERGOLINIC ALKALOIDS

[75] Inventor: Giorgio Ferrari, Milan, Italy

[73] Assignee: Simes Societa Italiana Medicinali e Sintetici S.p.A., Milan, Italy

[21] Appl. No.: 931,296

[22] Filed: Aug. 4, 1978

[30] Foreign Application Priority Data

Aug. 12, 1977 [CH] Switzerland ............... 9916/77

[51] Int. Cl.$^2$ .............................................. C07J 9/00
[52] U.S. Cl. .............................................. 260/397.25
[58] Field of Search ...................... 260/397.25, 397.2

[56] References Cited

U.S. PATENT DOCUMENTS

| 3,795,686 | 3/1974 | Ferrari et al. | 260/397.2 |
| 3,828,082 | 8/1974 | Canonica et al. | 260/397.2 |

*Primary Examiner*—Elbert L. Roberts
*Attorney, Agent, or Firm*—Cushman, Darby & Cushman

[57] ABSTRACT

A method is disclosed for extracting lysergol and ergolinic alkaloids from seeds of plants belonging to the Convulvulaceae family, Ipomoeae section, *petaloidea* genus (Choisy). The process applies to ground and defatted seeds and, after an orderly sequence of extraction, filtrations and crystallization, a first insoluble fraction is obtained, which contains the expected ergoline alkaloids and lysergol, whereafter a second sequence of extractive operations is carried out in order to separate as discrete fractions, the ergolinic alkaloids on the one hand, and the lysergol on the other hand.

18 Claims, No Drawings

PROCESS FOR THE PREPARATION OF POLYHYDROXYLATED STEROIDS, LYSERGOL AND ERGOLINIC ALKALOIDS

The present invention concerns a process for the extraction of certain substances which belong to the polyhydroxylated steroid class, also known as phytoecdisones, and to the ergolic alkaloids class. More specifically, the method according to the present invention regards the obtaining of crustecdisone, makysterone A, ecdisone, muristerone, lysergol, chanoclavine and other ergoline alkaloids.

Among the above-mentioned products, the first four belong to the class of the hormones of the metamorphosis of insects and can be characterized as follows:

(1) crustecdisone, that is, 2beta, 3beta, 14alpha, 20/R, 22/R, 25-hexahydroxy-5-beta-colest-7-en-6-one, having the formula:

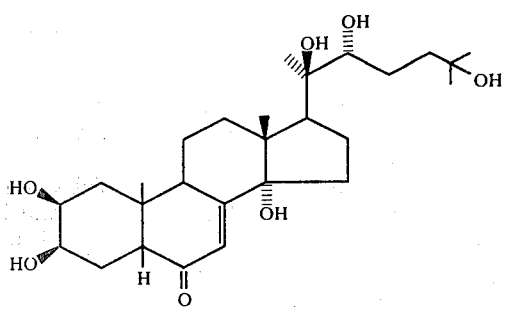

Such hormone was isolated in the past for the first time from a crustacean, *Jasus calandei* (Chem. Com. 1966, page 37) in the amount of 2 mg of pure hormone from 1 ton of crustacea. Its presence has been found also in *Bombyx mori*, together with ecdisone.

It is furthermore present in the insect *Antharea pernyi* (200 mg from 31 kg of pupa).

It has been isolated from the plants of *Podocorpus elatus*, impure with sterols (Chem. Com. 1966, page 905), in the amount of 0.05% of the weight of the vegetal material (Chem. Com. 1968, page 971): it is also present in *P.macrophyllus* (Tele 1968, page 3883).

It is also present in *Polypodium vulgare L.* (0.07–1.0% dry weight) (Phytochemistry 9, 1247 (1970)).

Moreover, makisterone A, that is, 2beta, 3beta, 14alpha, 20/R, 22/R, 25-hexahydroxy-24-methyl-5-beta-colesten-7-en-6-one, having the formula:

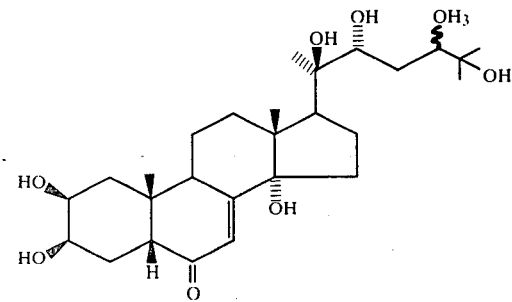

has been found in *Podocorpus macrophyllus* in the amount of 0.001% (T.Lett. 1969, page 3887).

In the family of the polyhydroxylated steroids, ecdisone, that is 2beta, 3beta, 14alpha, 22/R, 25-hexohydroxy-5beta-colest-7-en-6-one, having the formula:

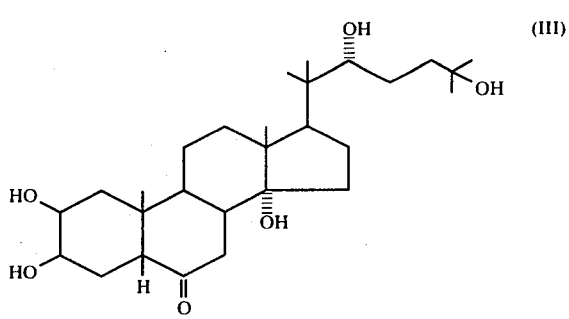

was the first to be isolated and identified (A. Butenandt, P. Karlson and Coll., Amm. Chem.662, 1 (1963)) and represented the starting point research conerning the properties of such steroids as regards the influence thereof in the biological cycle of insects. Finally, in recent years a new steroid has been identified and obtained, muristerone, that is, 2beta, 3beta, 5beta, 11alpha, 14alpha, 20/R, 22 R-heptahydroxy-5beta-colest-7-en-one having the formula:

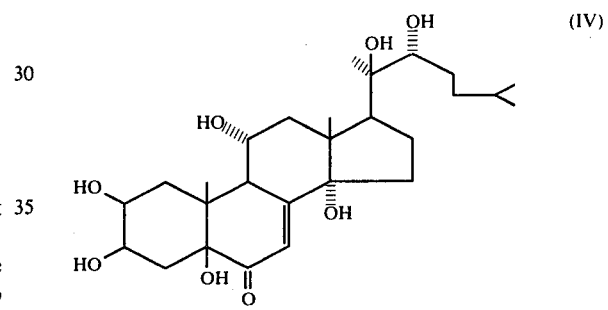

All such steroids, in their capacity as hormones, controlling the metamorphosis of insects, have found prevalent application as insecticides, both as such and/or in combination.

As regards lysergol and chanoclavine, they are ergolinic alkaloids, especially useful as intermediates in the production of drugs, and have long been well-known in the art.

It has now been found, and this forms the main subject matter of the present invention, that polyhydroxylated steroids and ergolinic alkaloids, particularly those above-mentioned, are contained in considerable amounts in a plant of the Ipomoea class (Convolvulaceae family), from which they can be extracted in an economically and industrially advantageous way, by means of the method of the present invention.

More specifically the method of the present invention, which has the purpose of obtaining the hormones of metamorphosis of insects and the above-identified ergoline alkaloids, is characterized by the fact that the extraction is carried out by starting from parts, particularly seeds, of *Ipomoea petaloidea* Choisy.

The process according to the present invention is thus characterized by the following operations:

(a) extraction with a solvent of the parts of Ipomoea petaloidea Choisy, in particular seeds, previously powdered and defatted, such solvent being selected from halogenated aliphatic hydrocarbons and their mixtures with aliphatic alcohols containing from 1 to 4 carbon atoms, and a base, such extraction being possibly repeated several times.

(b) concentration to low volume, at a temperature lower than 40° C., of the extract, or the combined extracts, which are then allowed to stand at a low temperature with separation of a precipitate (total crystallizate) and a supernatant phase;

(c) repeated washing with water of the total crystallizate, thus obtaining an insoluble fraction and an aqueous solution;

(d) washing with methanol of the insoluble fraction thus obtaining insoluble residue (alkaloidal fraction), which is combined with said supernatant phase, and a methanolic solution which, combined with said aqueous solution, forms the steroidal fraction;

(e) treatment of the alkaloidal fraction to isolate and purify lysergol and chanoclavine;

(f) treatment of the steroidal fraction to isolate the hormones of the metamorphis of insects.

According to the invention, the seeds of Ipomoea petaloidea Choisy are powdered so as to obtain a meal. The powdered drug is subsequently in cold conditions with petrol or light naphta (for ex. 80°-90° C.) in order to separate all the fats. The operation is repeated to complete exhaustion, which is obtained by repeating such operation three or four times.

The defatted drug then undergoes extraction with solvents suitable for removing the active principles. Especially useful for such purpose are the aliphatic halogenated hydrocarbons such as, for example, chloroform, carbon tetrachloride, methylene chloride, trichloroethylene. In order to facilitate the extraction the employment of a mixture of the aliphatic halogenated hydrocarbon with a small percentage of an aliphatic alcohol of low molecular weight (1-4 carbon atoms) is preferred. Among the alcohols which are useful for such purpose mention can be made of methyl, ethyl, isopropyl alcohol whilst, among bases, ammonia and amines are preferred. The added amounts of alcohols can reach 15%, whilst, the alkaline bases can reach 5% by volume with respect to the chlorinated hydrocarbon.

In the case of the preferred mixture, that is, chloroform-methanol-ammonia, the corresponding volumetric ratios are 9:0, 9:0,1.

The extraction is preferably carried out in a temperature range of from 10° to 50° C., whilst the number of extractions necessary for the exhaustion of the drug is comprised between three and five. The extraction, in each case, is repeated until Liebermann's test for steroid identification is negative.

The combined extracts are evaporated at a temperature lower than 40° C. to a tenth of their initial volume and allowed to stand for some days at a temperature of 0°-4° C. A precipitate (total crystallizate) is thus obtained, which represents the sterol fraction of the drug, and also the mother liquors containing part of the alkaloids of the starting drug. The total crystallizate undergoes repeated washings with water to an insoluble fraction and to an aqueous solution. The water-insoluble fraction, still wet, is washed with methanol, thus leading to an insoluble fraction, formed by the main part of the alkaloid fraction of the drug. The methanolic solution is in turn evaporated to dryness and the residue, repeatedly crystallized from water, leads to pure ecolisone.

The aqueous solution obtained from the washings of the total crystallizate is, instead, mixed with the same volume of methanol. After allowing to stand, a crystalline precipitate is obtained, which—on thin layer chromatography—proves to consist of makisterone A and ecdisterone. This precipitate, several times crystallized from methanol, provides pure makisterone A; in its turn, the hydromethanolic solution left from the separation of the crystalline precipitate (makisterone A+ecdisterone) is evaporated to dryness and chromatographed on alumina, thus forming a fraction mainly comprising muristerone.

The residual mother liquors from the crystallization of ecdisone or makisterone A, after evaporation to dryness, provide two residues which are combined and, by simple crystallization from acetone, provide crustecdisone or ecdisterone.

On the alkaloidal fractions of extraction of the drug, on the other hand, separation and isolation of the ergolinic alkaloids is carried out, utilizing aqueous solutions of acids. It has been found that diluted aqueous solutions of phosphoric acid prove particularly suitable. The extraction of the organic phase with aqueous solutions of acids is continued until Ehrlidh's test for alkaloids is negative.

From the collected acid extracts, weakly alkanilized with a base (preferably aqueous ammonia), the alkaloids are extracted again with a mixture of a chlorinated aliphatic hydrocarbon and an aliphatic alcohol. Particularly suitable is a mixture of chloroform/methanol in the volume ratio 7:3.

The extractions are repeated until Ehrlich's test proves negative. The collected extracts are washed with water once, dried on anhydrous sodium sulphate and then evaporated to dryness, at a temperature lower than 30° C., under low pressure. The residue proves to be formed of the alkaloidal fraction of Ipomoea petaloidea Choisy and shows when examined by thin layer chromatography, utilizing as solvent methylene chloride-methanol-benzol (25:5:5), and, as detector, a 3% solution of vanillin in alcohol with 0.5 in volume of concentrated sulphuric acid, after activation for 5 minutes at 110°-120° C., the presence of various ergolinic alkaloids, among which mainly lysergol, and secondarily chanoclavine.

It has been found that lysergol can be isolated from the total alkaloids by simply washing the mass with a lower aliphatic alcohol such as methanol, thus forming the insoluble residue in cold conditions. Such residue, after filtration, can be further purified by crystallization from a suitable organic solvent, or from a dimethylsulphoxide-water mixture. Lysergol can be particularly well purified by repeated crystallizations from dimethylsulphoxide-water 1:1. The product obtained in this way shows the following characteristics: on centesimal analysis it corresponds to the empirical formula $C_{16}H_{18}ON_2$: C% calc., 75.55; H%, 7.14; N%, 11.02. C% found, 75.39; H%, 7.22; N%, 10.96.

P. M. 254.3; m.p. (crystallized from alcohol) 253°-255° C. (with dec.); $[\alpha]_D^{20} = +54°$ (c=0.3 in pyridine.

The present invention also provides for the further isolation of chanoclavine from the residue containing the total ergolinic alkaloids after the isolation of lysergol. For such purpose, the present invention provides for the following further operations:

(a) evaporating to dryness in vacuo and at temperatures lower than 60° C., the residual mother liquors from the extraction of lysergol;

(b) dissolving the residue in pyridine in excess and adding acetic anhydride in an amount by weight equal to that of the dry residue, allowing the mixture to stand for 24 hours;

(c) precipitating crude chanoclavine diacetate by pouring the reaction product thus obtained over an excess of water and ice; and (d) purifying the crude chanoclavine diacetate after drying by recrystallization from ethyl acetate.

The thus obtained chanoclavine diacetate shows the following characteristics:

m.p. 172°–173° C.—$[\alpha]_D^{20}$ −53.4° (c=0.95 in pyridine)

$[\alpha]_D^{20}$ −58° (c=1% in chloroform)—I.R. spectrum in $CHCl_{31}$, characteristic absorption bands, at 1625 cm$^{-1}$ (N—$COCH_3$); 1730 cm$^{-1}$ (O—$COCH_3$)—U.V. spectrum in MeOH+ +1% $CHCl_3$: $\lambda_{max}$ 283 nm (log $\epsilon$3.81); 216 nm (log $\epsilon$4.76): 291 nm (log $\epsilon$3.78)

centesimal analysis for $C_{20}H_{24}O_3N_2$ (340.4) calc. C% 70.6; H% 7.1; N% 8.2. found 70.3 7.15 8.3.

As regards the steps of the above identified process the following should be noted:

(1) the dry residue obtained by evaporation of the mother liquors collected from the extraction of lysergol, is weighed and dissolved, preferably in about three times its weight of anhydrous pyridine;

(2) the excess of water and ice for the precipitation of the chanoclavine diacetate is about ten times the volume of the reaction product in step (b);

(3) the crude chanoclavine diacetate precipitate is separated by filtration after repeated washings with water and then purified.

The following examples are provided, solely to illustrate the invention without in any way limiting it:

EXAMPLE 1

40 kg of seeds of Ipomoea petaloidea Choisy are ground in a mill in order to obtain a meal with particle size comprised between 40 and 60 mesh per cm.

The ground drug is exhausted in cold conditions in an extractor provided with agitator 5 times, with petrol, b.p. 80°–90° C. 150 liters of solvent are employed each time. Each extractor lasts 3 hours, under agitation. The defatted drug, after complete removal of petrol, is twice extracted in the same apparatus with a mixture of chloroform-methanol-ammonia=9:0.9:0.1.

160 Liters of mixture are employed. Subsequently the mass is extracted a further three times with chloroform alone (100 liters). The collected extracts are concentrated at low pressure, at a temperature lower than 30° C. to a volume of 25 liters. The concentrate is allowed to stand in a refrigerator at 0°–4° C. for two days. The separated solid (total crystallizate) is filtered by pumps and the panel is dried in vacuo. The dried panel (300/400 g) is suspended in cold water 10 times its weight and agitated for 1 hour. The insoluble residue is filtered again, dissolved in methanol, three times its weight, and the methanolic solution is added to the main filtrate.

The filtrate is now washed with six liters of water in a separator. The organic phase is then further concentrated to a volume of eight liters, in vacuo at a temperature lower than 30° C. Such concentrate is exhausted by extracting it four times with a 5% phosphoric acid solution. In all, eight liters of acid solution, are employed. The collected acid extracts are alkalinized slightly with aqueous ammonia to pH 8 and exhausted by extracting with a mixture of chloroform/methanol=7:3. Four extractions are carried out, and in all eight liters are employed.

The organic extracts are washed once with water, then dried on anhydrous sodium sulphate and evaporated to dryness, under low pressure at a temperature lower than 30° C.

The residue (200–270 g) formed by the total ergolinic alkaloids of the drug has the composition indicated in the introductory part of this specification and is now agitated in cold conditions with 500 g of methanol for 1 hour. The insoluble part is filtered and dried in vacuo.

Further purification of the insoluble fraction (lysergol) is carried out by dissolving the crude product in an equal amount of dimethylsulphoxide slightly heating in a water bath. The solution is treated with decolourizing carbon, carefully filtered and to the filtrate there is added the same volume of distilled water. Then it is left under crystallization. The crystallized product is separated by filtration and dried in vacuo to constant weight.

The operation is repeated to obtain a product having the characteristics indicated in the introductory part.

EXAMPLE 2

The methanolic mother liquors obtained from the washings of the total ergolinic alkaloids identified in EXAMPLE 1, are placed in a rotary evaporator and the solvent is completely removed in vacuo to dryness at a temperature lower than 60° C. The residue (70–90 g) is taken up with anhydrous pyridine (210–270 ml) and (70–90 ml) acetic anhydride is added to the solution. The mass, protected from humidity, is allowed to stand for 24 hours. Subsequently it is poured onto ice and water (2000–2200 ml). The separated product is allowed to decant and repeatedly washed with water. It is filtered in vacuo, dried and recrystallized from ethyl acetate (30–45 g). The chanoclavine diacetate thus obtained proves pure, when examined by thin layer chromatography on Kieselgel $GF_{254}$ (Type 60), using methylene chloride-benzene-methanol 25:5;5 as solvent, and vanillin/sulphuric acid as reagent.

EXAMPLE 3

40 kg of seeds of Ipomoea petaloidea Choisy, finely ground, defatted by threefold agitation with 70 liters of light petrol (b.p. 30°–60° C.). The defatted drug was extracted three times with 120 liters of a mixture of $CHCl_3$/MeOH/$NH_4OH$ (9:0.9:0.1), for 12 hours, under agitation and at room temperature, and three times with 100 liters of $CHCl_3$; the combined extracts were concentrated to 1/10 of their volume at 40° C. The solid precipitate separating after 4–5 days in a refrigerator, was collected, washed with $CHCl_3$ and dried. From the mother liquors, after concentration, further solid deposited after storage in a refrigerator, this precipitate was also collected, washed with $CHCl_3$ and dried. The amount of combinated solids (fraction A) was 231 g. The mother liquors contained alkaloids (75 g) and further compounds belonging to fraction A. These latter were isolated by means of direct extraction with water and the residue, after evaporation to dryness (55 g) was combined with fraction A (in all, 336 g).

Fraction A was triturated 4 times with water (1500 ml) at 25° C. for one hour. The insoluble part (90 g) contained the alkaloids, whilst the dissolved product, after evaporation to dryness (fraction B, 250 g) mainly contained phytoecdisones. Fraction B was triturated four times with water (1000 ml) at 25° C. for 1 hour. The combined filtrates, after addition of MeOH, were concentrated under low pressure at 35° C. to about one fifth of the initial volume, allowed to crystallize in an ice bath, collecting the crystalline fraction C (50 g). From fraction C, after dissolution in methanol containing 1% water, crystals of reasonably pure makisterone A, 10 g, deposited, whilst crustecdisone remained in the mother liquors from which it was obtained by means of evaporation of the solvent (Residue $R_1$). The residual mother liquors from precipitation of crystalline fraction C were evaporated to dryness (110 g) and chromatographed on silica gel column (Merck, 1000 g), collecting and combining the fractions eluted with EtOAc. After evaporating to dryness, such fractions were dissolved in EtOAc and left to crystallize, thus providing muresterone (10 g). From the subsequent fractions eluted with a mixture of EtOAc and 10% methanol, crustecdisone was obtained (20 g).

The water-insoluble part of fraction B, still wet after the treatment in water, was triturated with methanol (200 ml) at 50° C. The insoluble part still contained alkaloids (9.5 g) whilst the soluble part D after evaporation to dryness at a temperature lower than 35° C., was repeatedly crystallized from water providing ecdisone (5 g) as a solid, whilst the mother liquors contained further crustecdisone, which was obtained by means of evaporation to dryness and crystallization (Residue $R_2$).

The two combined residues $R_1$ and $R_2$ were recrystallized from metallic carbonate thus providing relatively pure crustecdisone (60 g).

Finally, the alkaloidal part of the extract in EXAMPLE 3 was treated as in EXAMPLES 1 and 2 to recover lysergol and chanoclavine whilst the steroidal fraction of EXAMPLE 1 was treated as in EXAMPLE 3 to recover each single phytoecdisone.

What I claim is:

1. In a process for the production of hormones of themetamorphosis of insects and for the production of ergolinic alkaloids the improvement comprising extracting said hormones and alkaloids from a plant of the Convolvulaceae family, Ipomoeae section, Petaloidea (Choisy) genus.

2. A process according to claim 1, characterized by the fact that the extraction is performed on the seeds, ground and previously defatted, with a chlorinated aliphatic hydrocarbon solvent, in a temperature range of from 10° to 50° C. and repeating the extraction 3-5 times.

3. A process according to claim 2, characterized by the fact that to said solvent there is added a small amount, not more than 15% by volume over the solvent itself, of an aliphatic alcohol of low molecular weight (having from 1 to 4 carbon atoms) and a small amount, not more than 5% by volume over the solvent, of a base selected from ammonia and amine.

4. A process according to claim 2, characterized by the fact that the extracts, which have been combined and concentrated to a tenth of their initial volume at a temperature lower than 30° C. and under low pressure, are left to stand for some days at 0°-4° C. and subsequently filtered off, thus obtaining a total crystallizate and mother liquors, said total crystallizate being washed with water, with separation of an insoluble residue and an aqueous solution, said insoluble residue being washed with methanol with separation of an insoluble phase and a methanolic solution, said insoluble phase together with said mother liquors undergoing separation of the ergolinic alkaloids by means of extraction with an acid aqueous solution in order to separate the ergolinic alkaloids, said extraction being continued until there is a negative Ehrlich's test for alkaloids; from the combined acid extracts, slightly alkalinized with a base, the alkaloids are re-extracted with a mixture of a chlorinated aliphatic hydrocarbon and an aliphatic alcohol, continuing such re-extraction until there is a negative Ehrlich's test, and the combined extracts, washed only once with water and dried on anhydrous sodium sulphate are evaporated to dryness at a temperature lower than 30° C. under low pressure, thus forming a residue comprising the alkaloidal fractions of the extracted plant wherein lysergol is mainly present.

5. A process according to claim 4, characterized by the fact that said acid aqueous solution is a phosphoric acid solution.

6. A process according to claim 4, characterized by the fact that said extraction mixture is a mixture of chloroform and methanol in volume ratio 7:3.

7. A process according to claim 4, characterized by the fact that lysergol is isolated from said residue by washing with lower aliphatic alcohol and further purified by crystallization with an organic solvent or a mixture of dimethylsulphoxide and water, preferably in the ratio 1:1.

8. A process for the extraction of ergolinic alkaloids according to claim 4, characterized by the fact that the mother liquors, which are residual from the lysergol isolation step, are evaporated to dryness in vacuo and at a temperature lower than 60° C., the dry residue is dissolved with an excess of anhydrous pyridine preferably about three times the weight of the dry residue and acetic anhydride is added in an amount equal to that of the residue, the reaction mixture is left to stand for 24 hours; chanoclavine diacetate is precipitated by pouring the mixture produced by the reaction into an excess of water and ice, preferably about 10 times in volume over the volume of the reaction product; crude chanoclavine diacetate is filtered and purified, after crystallization, by recrystallization from ethyl acetate.

9. A process according to claim 1, for the extraction of pure polyhydroxylated steroids, characterized by the fact that from said methanolic solution, after evaporation to dryness, a residue is obtained, which, after repeated crystallizations from water, provides pure ecdisone and mother liquors.

10. A process according to claim 1 for the extraction of polyhydroxylated steroids, characterized by the fact that said aqueous solution is treated with methanol in a ratio of 1:1, with separation of a crystallizate, or insoluble phase, containing molesterone A and crustecdisone and of mother liquors containing murosterone.

11. A process according to claim 1, characterized by the fact that from said crystallizate or insoluble phase pure makisterone A is isolated by repeated crystallizations from methanol, thus providing a hydroalcoholic solution containing ecdisterone.

12. A process according to claim 1, characterized by the fact that said hydroalcoholic solution and said residual mother liquors from the separation of ecdisone are evaporated to dryness and from the combined residues, by crystallization from acetone, they provide ecdisterone or crustecdisone.

13. A process according to claim 1, characterized by the fact that from said mother liquors containing muristerone, by evaporation to dryness and chromatography on alumina, muristerone is obtained.

14. A process according to claim 8 wherein the alkaloid extracted is chanoclavine.

15. A process according to claim 9 wherein the steroid extracted is pure ecdisone.

16. A process according to claim 2 wherein the solvent is chloroform, carbon tetrachloride, methylene chloride or trichloroethylene.

17. A process according to claim 1 wherein the hormones and ergolinic alkaloids produced are selected from the group consisting of crustecdisone, makisterone A, ecdisone, muristerone, lysergol and chanoclavine.

18. A process according to claim 17 wherein the solvent is selected from the group consisting of chloroform, carbon tetrachloride, methylene chloride and trichloroethylene.

* * * * *